(12) United States Patent
Llop

(10) Patent No.: US 10,952,824 B2
(45) Date of Patent: Mar. 23, 2021

(54) MULTI-PIECE ABUTMENT AND DIGITAL METHOD FOR PREPARATION OF A DENTAL IMPLANT SURGICAL SITE FOR THE PROMOTION OF A DESIRED EMERGENT SULCUS

(71) Applicant: NATIONAL DENTEX, LLC, Palm Beach Gardens, FL (US)

(72) Inventor: Daniel R. Llop, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 263 days.

(21) Appl. No.: 15/667,575

(22) Filed: Aug. 2, 2017

(65) Prior Publication Data

US 2018/0036103 A1 Feb. 8, 2018

Related U.S. Application Data

(60) Provisional application No. 62/475,203, filed on Mar. 22, 2017, provisional application No. 62/370,177, filed on Aug. 2, 2016.

(51) Int. Cl.
*A61C 8/00* (2006.01)
*A61B 34/10* (2016.01)

(52) U.S. Cl.
CPC ............ *A61C 8/0042* (2013.01); *A61B 34/10* (2016.02); *A61C 8/008* (2013.01); *A61C 8/0068* (2013.01);
(Continued)

(58) Field of Classification Search
CPC .... A61C 8/0042; A61C 8/0077; A61C 8/0068
See application file for complete search history.

(56) References Cited

U.S. PATENT DOCUMENTS 5,069,622 A * 12/1991 Rangert ................. A61C 8/005
433/173
5,662,474 A * 9/1997 Jorneus ................. A61C 8/005
433/172
(Continued)

FOREIGN PATENT DOCUMENTS

WO  WO 2012/158769 A1  11/2012

OTHER PUBLICATIONS

International Search Report and Written Opinion dated Nov. 13, 2017 for Application No. PCT/US2017/045179, 12 pgs.
(Continued)

*Primary Examiner* — Ralph A Lewis
(74) *Attorney, Agent, or Firm* — Frost Brown Todd LLC

(57) ABSTRACT

A patient-specific dental implant abutment may comprise an abutment base that attaches to a dental implant, the abutment base comprising a base top, a base bottom, and a base side, the base side continuously connecting the base top and base bottom together, the abutment base constructed to removably attach to a dental implant. The device may further comprise a set of abutment caps, each abutment cap comprising a cap top connected to the cap bottom, the cap bottom removably attaching to the top of an abutment base in a manner that the cap top does not contact an emergent sulcus, wherein each abutment cap has a different cap top that is constructed to handle at least one function relating to a phase of a dental implant surgery.

19 Claims, 6 Drawing Sheets

(52) U.S. Cl.
CPC ... *A61B 2034/102* (2016.02); *A61B 2034/105* (2016.02); *A61B 2034/108* (2016.02); *A61C 8/0053* (2013.01); *A61C 8/0089* (2013.01)

(56) References Cited

U.S. PATENT DOCUMENTS

| | | | |
|---|---|---|---|
| 5,810,592 A * | 9/1998 | Daftary | A61C 8/005 433/172 |
| 6,386,876 B1 * | 5/2002 | Lee | A61C 8/0001 433/173 |
| 6,663,388 B1 * | 12/2003 | Schar | A61C 8/005 433/173 |
| 9,004,919 B2 | 4/2015 | Llop | |
| 9,173,723 B2 | 11/2015 | Harrison | |
| 9,226,801 B2 | 1/2016 | Groscurth et al. | |
| 9,259,297 B2 * | 2/2016 | Ilter | A61C 8/0001 |
| 9,364,299 B2 | 6/2016 | Marlin | |
| 9,408,678 B2 | 8/2016 | Harrison | |
| 9,498,307 B2 | 11/2016 | Harrison | |
| 9,504,533 B2 | 11/2016 | Groscurth et al. | |
| 9,554,879 B2 | 1/2017 | Harrison | |
| 2009/0117520 A1 * | 5/2009 | Kikuchi | A61C 8/005 433/174 |
| 2009/0298008 A1 | 12/2009 | Groscurth et al. | |
| 2010/0124731 A1 | 5/2010 | Groscurth et al. | |
| 2011/0045431 A1 | 2/2011 | Groscurth et al. | |
| 2011/0045432 A1 | 2/2011 | Groscurth et al. | |
| 2012/0322030 A1 | 12/2012 | Fromovich | |
| 2013/0196290 A1 * | 8/2013 | Herrington | A61C 8/006 433/173 |
| 2014/0272778 A1 | 9/2014 | Llop | |
| 2016/0106517 A1 | 4/2016 | Groscurth et al. | |
| 2016/0324599 A1 | 11/2016 | Harrison | |
| 2017/0071697 A1 | 3/2017 | Groscurth et al. | |
| 2017/0112592 A1 | 4/2017 | Groscurth et al. | |

OTHER PUBLICATIONS

U.S. Appl. No. 62/370,177, filed Aug. 2, 2016.
U.S. Appl. No. 62/475,203, filed Mar. 22, 2017.

* cited by examiner

MULTI-PIECE ABUTMENT AND DIGITAL METHOD FOR PREPARATION OF A DENTAL IMPLANT SURGICAL SITE FOR THE PROMOTION OF A DESIRED EMERGENT SULCUS

CROSS-REFERENCE TO RELATED APPLICATIONS

This application claims the benefit of U.S. Provisional Patent Application No. 62/475,203, filed on Mar. 22, 2017 and U.S. Provisional Patent Application No. 62/370,177 filed on Aug. 2, 2016. The disclosures of both applications are incorporated herein by reference in their entirety as set forth in full and for all purposes.

FIELD OF THE DISCLOSURE

The present disclosure generally relates to those dental systems and digital methods as used in creating patient-specific virtual maps and models of a patient's mouth. More particularly, to those dental systems and digital methods for using such virtual patient specific maps and models in determining and bringing about the optimization of a desired real life profile of the removed tooth's emergent sulcus utilizing dental implant technology.

BACKGROUND

As a person continues to age, tooth loss inevitably occurs and tooth replacement, as provided by the dental profession, is often employed to make up for the tooth loss. One of the more important aspects of this tooth replacement procedure could be a sulcus (e.g., soft tissue complex that is impacted by hard tissue/bone structure of the mouth) as attached to the cortical occlusal bone that generally results in free gingival margin (e.g. the gum line surrounding the cavity formed when the tooth was lost or formed around the lost tooth's replacement crown) changes once the natural tooth is removed. In some dental cases, the bone portion (or hard tissue) of the mouth where the tooth was formerly anchored through the normal healing process can compact upon itself and as a result change the bone line, while the gum tissue from that portion of mouth can also recede or become thinner, thus changing the overall profile of cortical plate or jaw shape. These changes may make the establishment of an implant surgical site (with a corresponding placement of a dental crown upon a dental implant at the implant surgical site) more difficult, especially in those areas such as the front of the mouth where the bone and tissue are much thinner structures with correspondingly less material in which to anchor the dental implant. This change in profile may effect a tooth replacement telemetry and other implant orientations for proper implant placement and anchorage. If these changes are not properly undertaken or otherwise properly corrected, the changes to the dental implant surgical site may ultimately place the affixed dental crown in a position within the mouth that would appear to be out of alignment or otherwise appear to be in an unnatural placement in relation to the surrounding teeth. As such, the newly attached crown may properly support the bite of the patient but may appear to have an unnatural orientation, calling attention to the crown, and thus defeating one of the cosmetic purposes of tooth replacement: that persons observing the patient's smile should not notice the occurrence of dental implant/tooth replacement.

What dentistry has attempted in the past is generally to use a healing abutment to manually rectify these changes in bone and sulcus and otherwise substantially improve the operation site for the placement of the implant. Such healing abutments substantially have a circular lateral cross section and a generic construction. These healing abutments are not patient-specific, much less tooth-specific. These generic healing abutments generally do not provide for proper encouragement and support of a sulcus whose resulting profile could match the base of the dental crown or match the overall presentation of the remaining teeth in a manner that is both healthy and esthetically pleasing.

In a dental operation to provide for implant-based tooth replacement the soft tissue is often cut and removed to designate the dental implant surgical site. The dental implant could then be secured to the implant surgical site with the bottom of the implant being substantially embedded into the bone. A healing abutment could then be attached to the exposed top portion of the dental implant. Once the tissue healing (and bone solidification/osseointegration around the buried/artificial root portion of the implant) has finalized, the healing abutment could be removed from the implant and be discarded. The final abutment could be attached to the implant in place of the healing abutment; the final abutment providing the structural support for the attachment of the crown. Procedures could then be utilized as needed to place and permanently secure the dental crown to the final abutment/dental implant combination.

However, if the sulcus did not heal properly or grew away from the abutment or dental implant and does not provide an appropriate or adequate free gingival margin (e.g., gum line) and the like, then additional surgical procedures may be implemented to manually sculpt the soft tissue (and possibly bone) as required to generally bring the sulcus into a proper orientation and profile to provide the required contact with the placed dental crown. These additional post-operative procedures could be costly, painful, and time-consuming.

Some embodiments of the present disclosure may be used prior to the dental surgery itself to alleviate the frequency and severity of these issues, for example a pre-surgical digital method and associated apparatus. A pre-surgical digital method and associated apparatus may include computer virtual modeling that utilizes and merges DICOM data sets taken from the patient's mouth—such as a CBCT scan (for the bone structure, root trajectory, and alike); optical scan data; scanned physical impressions/castings (for tissue structure); digital impression; and the like—to create a virtual, patient-specific model or map of a profile for the desired emergent sulcus for the dental implant surgical site. Using this patient-specific digital data, a temporary (e.g., disposable) patient-specific healing abutment can be virtually designed to meet a desired emergent sulcus profile. By virtually modeling such a virtual healing abutment upon a virtual implant body at a virtual implant operation site, the dimensions of the proposed actual patient-specific healing abutment can be confirmed to ensure that such a patient-specific healing abutment could: properly encourage the actual development of the projected desired emergent sulcus profile; properly support the developed sulcus profile once emerged; and help ensure that the resulting emergent sulcus profile could properly accommodate a placed crown. In this manner virtual modelling can be used to ensure that the crown's final appearance, placement, and support complement the patient's natural overall sulcus profile and gingival harmony by confirming the overall use of the implant, the design of the patient-specific healing abutment configured to bring about a planned emergent sulcus profile, and the design and placement of the final abutment.

Additionally, some embodiments of the present disclosure may eliminate the need for a final abutment—separate from the healing abutment—by providing for a multiple-piece abutment comprising a base and a cap that removably attaches to a top of the base. In some embodiments of the present disclosure, a base could be patient-specific, digitally designed, and manufactured to substantially encourage the development of and support of the emergence of a sulcus with a desired profile to receive a bottom portion of a replacement crown. A cap, in some embodiments, could be selected from a set of interchangeable caps, each cap further providing a separate and different function needed during the dental implant surgery. The various cap functions may include, alone or in any combination thereof: acting as an implant driver attachment, protecting the spacing over a dental implant surgical site as defined by the teeth on each side of the dental implant surgical site, providing an attachment support for a restorative crown, serving as an angled attachment support to support a restorative crown where sufficient bone tissue is limited, and performing other functions that may relate to dental implant surgery or other tooth replacement processes. According to some embodiments of the present disclosure, a base could be affixed to an implant and then a cap could be selected and attached to the base to provide the desired function. As the tooth-replacement process moves to a different surgical stage, an attached cap could be exchanged with another cap, providing a different function as needed or desired in that particular surgical stage. This swapping of caps could generally alleviate the need to remove the patient-specific sulcus healing base that otherwise continuously encourages the formation of a specific emergent sulcus profile.

SUMMARY

Advantages of One or More Embodiments

The various embodiments of the present invention may, but do not necessarily, achieve one or more of the following advantages:

to provide a computer-generated virtual model of a patient's mouth to compare an implant surgical site with its mirror site/location on the contralateral side of the patient's mouth and thereby permit the generation of an emerging sulcus profile for an implant surgical site that would be biologically correct and esthetically pleasing when a dental crown is finally fitted to the surgical site;

to provide a virtual model specific to a patient's mouth including a biologically-correct shape and position for an implant surgical site that consequently provides a dental healthcare professional with the ability to plan (e.g., pre-operatively and virtually) an implant surgery that may include designing a profile for an emergent sulcus to create a concavity or tooth socket;

the ability to use virtual mapping and modeling (e.g., Rapid Prototyped CAD/CAM) to manufacture a patient-specific healing abutment designed to promote a specific emergent sulcus profile at an implant surgical site;

to provide a specifically engineered patient-specific healing abutment at an implant surgical site to assist the promotion of a desired emergent sulcus;

the ability to use patient-specific, healing abutment dimensions to further design and manufacture a final abutment upon which a final crown may be permanently affixed, where a base of the final abutment and the final crown correspond to a desired emergent sulcus profile;

to provide a multiple-piece abutment whose base may stay in continuous contact with a sulcus after an implant is placed and whose caps are subsequently swapped out to aid in accomplishing different tasks in an implant surgical procedure;

the ability to use a multiple-piece abutment to drive an implant into a dental implant surgical site; and to provide a mechanical connection between a multiple piece abutment and an implant operable to transfer a rotational or torsional force to the implant in a manner that is distinct from that applied to a connection between a single piece abutment and an implant.

These and other advantages may be realized by reference to the remaining portions of the specification, claims, and abstract.

BRIEF DESCRIPTION OF ONE EMBODIMENT

One possible embodiment of the invention could be a patient-specific dental implant abutment that conforms to a proposed emergent sulcus profile for a dental implant surgical site, comprising: an abutment base that attaches to a dental implant, the abutment base comprising a base top, a base bottom, and a base side, the base side continuously connecting the base top and base bottom together, the abutment base constructed to removably attach to a dental implant, the base side providing an emergent sulcus profile created from the comparison of a first data from a first site map of a dental implant surgical site of the specific patient's mouth with a second data of the virtual model of the specific patient's mouth pertaining to a second site map of the mirror location of the dental implant surgical site, the mirror location being on the contralateral side of the specific patient's mouth from the dental implant surgical site, the data comparison using a reverse image of the mirror location second site map being overlaid upon the first site map of the dental implant surgical site; a set of the abutment caps, each abutment cap comprising: a cap top connected to the cap bottom, the cap bottom removably attaching to the top of an abutment base in a manner that the cap top does not contact an emergent sulcus, wherein each abutment cap has a different cap top that is constructed to handle at least one function relating to a phase of a dental implant surgery.

Another possible embodiment of the present invention could be a method of creating a proposed emergent sulcus profile for a dental implant surgical site, comprising: obtaining data of a patient's mouth needed to create a computer-generated virtual model of the patient's mouth; processing said obtained data to create the computer-generated virtual model of the patient's mouth; comparing virtual-model data as it pertains to a first site map of a dental implant surgical site of the patient's mouth with other virtual-model data as it pertains to a second site map of a mirror location of the dental implant surgical site, the mirror location being on the contralateral side of the patient's mouth from the dental implant surgical site, creating and allowing a mirror image of the second site map of the mirror location to be overlaid upon the first site map of the proposed dental implant surgical site; creating from that comparison of virtual-model data, an emergent sulcus profile for the dental implant surgical site; using the emergent sulcus profile for creating a multiple-piece patient-specific abutment that comprises a set of abutment caps and an abutment base, the abutment cap removably attaching to the top of an abutment base in a manner that the abutment cap does not contact the emergent sulcus at the dental implant surgical site, the abutment base supporting the emergent sulcus of the dental implant surgical site to develop and support the emergent sulcus pursuant to the proposed emergent sulcus profile, wherein each abutment cap has a different cap top that supports a function of the dental implant surgery.

Yet another possible embodiment could be a patient-specific dental implant abutment comprising: an abutment base that attaches to a dental implant, the abutment base comprising a base top, a base bottom, and a base side, the base side continuously connecting the base top and base bottom together, the abutment base constructed to removably attach to a dental implant; a set of abutment caps, each abutment cap comprising a cap top connected to the cap bottom, the cap bottom removably attaching to the top of an abutment base in a manner that the cap top does not contact an emergent sulcus, wherein each abutment cap has a different cap top that is constructed to handle at least one function relating to a phase of a dental implant surgery.

The above descriptions set forth, rather broadly, a summary of multiple embodiments of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phrasing and terminology employed herein are for the purpose of description and should not be regarded as limiting.

DETAILED DESCRIPTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
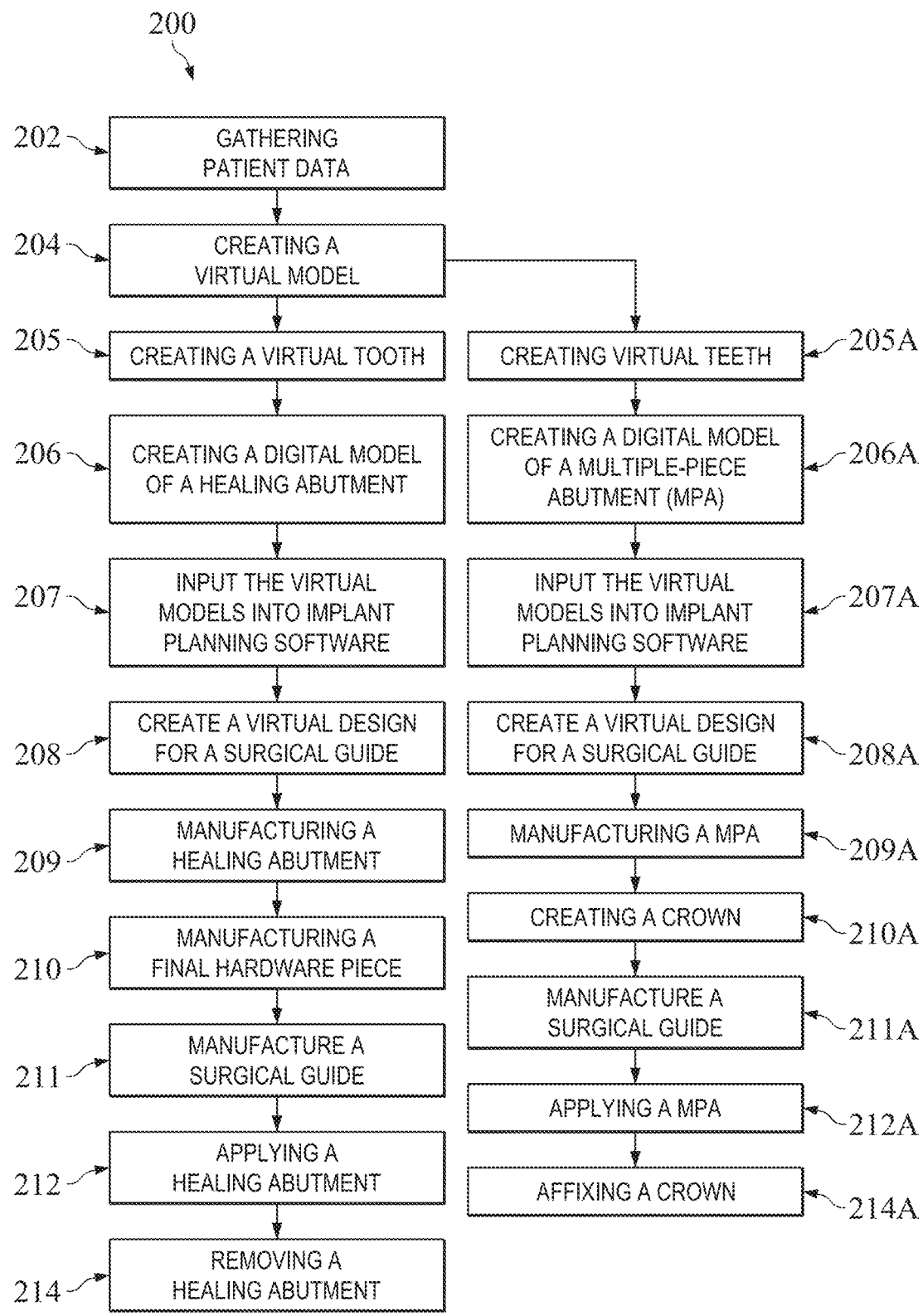
FIG. 1 illustrates a flow chart of a method of virtually modeling a patient's mouth, according to one embodiment of the disclosure.

As shown in FIG. 1, according to some embodiments of the present disclosure a method 200 may be implemented prior to a dental implant surgery (i.e., pre-surgical) including virtual modeling (e.g., a virtually created model) of a patient's mouth to further develop a patient-specific, Added Manufacturing or CAD/CAM profile/model of an emergent sulcus at a proposed implant surgical site. This virtual profile could be used to create a variety of patient-specific pieces of implant hardware, including a patient-specific healing abutment 20 (e.g., one embodiment of which is substantially shown in FIG. 2), a patient-specific final abutment 40 (e.g., one embodiment of which is substantially shown in FIG. 3), or a patient-specific crown 50 (e.g., one embodiment of which is shown in FIG. 4). According to some embodiments, any one or combination of a variety of patient-specific pieces of implant hardware could be used to first bring about, and then later support, an emergent sulcus having a desired profile. In some embodiments, a virtual profile could be used to create a concavity that may be used in the manufacture of a patient-specific healing abutment 20. Additionally, one or more dimensions of a patient-specific healing abutment 20 may be used to create a patient-specific crown 50 or a patient-specific final abutment 40, according to some embodiments. According to some embodiments dental implant components (e.g., once attached to a dental implant at an implant surgical site) may contribute to the formation of a desired emergent sulcus proximate to a surgical implant site. For example, in accordance with a virtual profile, they may generally control an augmentation of soft and hard tissues at the surgical implant site and then further supporting the emergent sulcus as it develops.

A method 200 may include gathering patient data 202. In some embodiments, gathering patient data 202 may include means of gathering data which are well known to those skilled in the art including, for example, the creation of physical models (e.g., dental castings, impressions) of a specific patient's mouth that may then be scanned and reduced to a first data set (e.g., a digital value). In some embodiments a patient's mouth may be digitally scanned to generate a first data set, with at least some of the first data set being appropriate for use in virtual mapping and modeling of the patient's mouth. Such scans could include a CBCT scan, an Optical Scan, or any other suitable scanning means. A first data set generated from a CBCT scan may include data relating to placement of hard tissue and root trajectory, while other scans (e.g., an Optical Scan, physical models) may generate a first data set relating to a tissue values and a tooth projection/free gingival margin. In some embodiments, after gathering patient data 202 is substantially completed, a method 200 may proceed to creating a virtual model of the patient's anatomy 204.

A virtual model may include all or a portion of a patient's mouth. Creating a virtual model 204, in some embodiments, may include combining a computing capability (e.g., a computer system), with an appropriate software modeling program generally known by those skilled in the art to process a first data set and generate a second data set. A second data set may include, according to some embodiments, a computer-supported (e.g., computer-generated), patient-specific, virtual model of the patient's mouth (e.g., desired portions of the patient's mouth). A second data set may include, in some embodiments, information relating to a first site map, a second site map, or both. A first site map may be a map of an dental implant surgical site. A second site map may be a map of a location in a patient's mouth that is not a dental surgical site. For example, in some embodiments a second site map may correspond to a location that is a mirror image of a dental implant surgical site (e.g., a first site map) and located on a contralateral side of a patient's mouth from the first site map. In some embodiments, creating a virtual model 204 may include comparing a first site map to a second site map. For example, a first site map may be compared to a second site map by creating a mirror or reversed image of the second site map and overlaying it upon the first site map.

According to some embodiments, creating a virtual model 204 may include comparing information from multiple site maps from multiple locations throughout a patient's mouth to generate a comparison data set. A comparison data set, in some embodiments, may be used to establish a desirable orientation or telemetry for implanting hardware (e.g., an implants, a crown) at a dental surgical site. In some embodiments, a comparison data set may be used to digitally map or plan a design of a crown (e.g., a base of a crown) to support a projected development profile of an emerging sulcus.

According to some embodiments, a virtual model, a second data set, a comparison data set, or any combination thereof may be used to establish a proposed emergent sulcus profile, which may denote how the development of an emergent sulcus could occur at a surgical implant site when supported by an abutment and later a crown. A proposed emergent sulcus profile may take into account specific architectures (e.g., anatomical, biological) of a dental surgical site's sulcus anatomy to accurately predict a final outcome of dental implant surgery in conjunction with an expected profile of the emergent sulcus. According to some embodiments, the virtual model of the patient's anatomy may also be used to create a virtual tooth 205 or virtual teeth 205A that fit the patient's arch form and shape. In some embodiments, creating a virtual tooth 205 may be followed by creating a digital model of a healing abutment 206. According to some embodiments, creating virtual teeth 205A may be followed by creating a digital model of a multiple-piece abutment 206A.

Creating a digital model of a healing abutment 206, in some embodiments, may include using a virtual model, a virtual tooth, a proposed emergent sulcus profile, or both, to create a model of a patient-specific concavity. A patient-specific concavity may be an opening or a tooth socket configured to support an insertion of an implant-abutment combination and a bottom portion of a dental crown and that may be surrounded by an emergent sulcus or soft tissue. According to some embodiments, creating a model of a patient-specific concavity may further include using digital data (e.g., a second data set, a comparison data set) to create a virtual model of a patient-specific healing abutment. After this, the virtual models of the patient anatomy, the virtual tooth or teeth, and the healing abutment are inputted into implant planning software 207, 207A. The implant planning software is used to determine the placement and angle of the implants to be fixed into the hard tissue (e.g., bone) in the patient's anatomy so that the abutment and crowns are fixed in the appropriate location to ensure stability, strength, and the desired cosmetic appearance. Based upon these factors, a virtual design for a surgical guide is created 208, 208A. The surgical guide is used to determine the proper angle and location for the pilot holes and eventually the fixation of the implant itself into the patient's anatomy. In some embodiments, creating a digital model of an abutment 206 (e.g., a healing abutment, a final abutment) may be followed by manufacturing an abutment 209, 209A (e.g., a healing abutment, a final abutment).

Manufacturing a healing abutment 209, 209A, in some embodiments, may include transferring a dataset generated in 204 (e.g., a virtual model dataset) or a dataset generated in 206 (e.g., a digital model dataset) to a suitable manufacturing means (e.g., a three dimensional printer) which, in some embodiments, may be controlled by a computing means, manufacturing programs, both a computing means and manufacturing programs, or by any other single or combination of controlling means. According to some embodiment, manufacturing a healing abutment 208 may include processing a dataset generated in 204 or 206 to create a patient-specific healing abutment. For example, manufacturing a healing abutment 208 may include processing a dataset generated in 204 or 206 to create a patient-specific healing abutment that is modeled and designed to bring about a desired profile of an emergent sulcus or soft tissue development when the healing abutment is subsequently attached to a dental implant at a dental implant surgical site.

According to some embodiments, a method 200 may further comprise manufacturing a final hardware piece 210 (e.g., a final abutment, a crown, both). Manufacturing a final hardware piece 210 may include transferring one or more data points (e.g., from a virtual model generated in 204, from a digital model of a healing abutment generated in 206, both) to a means of computing/manufacture (e.g., a three dimensional printer) to generate a final hardware piece (e.g., a patient-specific final abutment, a patient-specific crown). Similar processes can be used to manufacture a surgical guide 211, 211A as described above with respect to the healing abutment or the final hardware piece. U.S. Patent Application Publication No. 2014/0272778, assigned to National Dentex, LLC and incorporated by reference into this application, describes a representative process for designing and manufacturing a surgical guide suitable for use with the described process.

According to some embodiments, a method 200 may further include applying a healing abutment 212, 212A. According to some embodiments, a healing abutment may be removably attached (e.g., by fastener, screw fastener, adhesive) to a top of a dental implant after the dental implant has been properly secured into a dental surgical site. In some embodiments, a healing abutment may be removably attached (e.g., by fastener) to a top of a dental implant to form a dental implant-abutment pair, and the dental implant-abutment pair may be securely fastened into a dental surgical site. A top of a healing abutment, in some embodiments, may be scalloped to provide edges that may contact one or more portions of a desired profile of emergent free gingival margin (e.g., the scalloping could help prevent patient interference with the dental surgical site and allowing proper/desired sulcus emergence to occur). In some embodiments, one or more sides of a healing abutment may contact one or more portions of an emergent sulcus, thereby providing support and aiding in formation of a desired emergent sulcus.

According to some embodiments, after insertion of a dental implant and applying a healing abutment 212, 212A or after insertion of a dental implant-abutment pair, the dental surgical implant site may be sutured. Suturing may aid in the proper formation of a desired emergent sulcus profile (e.g., by minimizing or eliminating any gaps between an initial sulcus and the healing abutment). In some embodiments a temporary retainer or temporary crown device (e.g., Temporary Fixed Partial Denture, Maryland Bridge, Snap on Smile, Essix Retainer, Flipper (Acrylic Removable Partial Denture)) may be inserted at a dental surgical site.

In some embodiments, a method 200 may include removing a healing abutment 214. For example, removing a healing abutment 214 may be performed after sufficient ossification of a bone material in which a dental implant was inserted and to which the healing abutment is attached. Removing a healing abutment 214, in some embodiments, may include removal of a tissue from one or more surfaces of the healing abutment. According to some embodiments, a tissue may include a thin, healthy keratinized tissue overgrowth formed over one or more surfaces of a healing abutment (e.g., a top) and removing the tissue may include using a laser or a scalpel. Removing a healing abutment 214, in some embodiments, may include unfastening (e.g., unscrewing, un-threading, un-snapping) the healing abutment from a dental implant. An unfastened healing abutment may be removed from a dental implant surgical site and, in some embodiments, may be discarded. In some embodiments, a healing abutment may be configured to be reusable or recyclable (e.g., a prefabricated design that may be sterilized and re-used).

According to some embodiments, removing a healing abutment 214 may further include attaching a final abutment to a dental implant. In some embodiments, a final abutment (e.g., patient-specific, pre-fabricated) may include a base having dimensions that substantially correspond to a healing abutment (e.g., patient-specific, pre-fabricated) such that the base of the final abutment sits adjacent to a formed sulcus and provides support to the sulcus (e.g., aiding in the maintenance of the sulcus shape and profile). A final abutment, in some embodiments, may be removably (e.g., screw fixation) or fixedly (e.g., adhesive) attached to a top portion of a dental implant.

According to some embodiments, removing a healing abutment 214 may further include removably (e.g., screw) or fixedly (e.g., adhesive) attaching a chimney 48 to a final abutment. In some embodiments, removing a healing abutment 214 may further include attaching (e.g., adhesive, screw) a crown to at least a portion of a chimney portion of a final abutment (e.g., patient specific, pre-fabricated). According to some embodiments, a crown may be permanently affixed (e.g., cemented) to a chimney of a final abutment (e.g., patient-specific, pre-fabricated). In some embodiments, upon substantial completion of removing a healing abutment 214, a method 200 may proceed back 216 to step 202 for use in another dental implant surgery (e.g., another dental surgical site).

Figure 2:
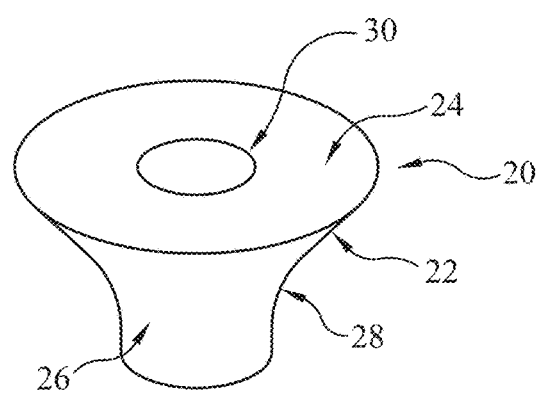
FIG. 2 illustrates a perspective view of a patient-specific healing abutment, according to one embodiment of the disclosure.

According to some embodiments, a healing abutment 20, as substantially shown in FIG. 2, may comprise a body 22 made of suitable, resilient material (e.g., pekton, peek, ceramics, alloys, titanium, gold, composites) and may include a top 24, a bottom 26, and a side 28, the side 28 substantially connecting the top 24 and the bottom 26 together. In some embodiments, a top 24 and a bottom 26 may be continuously connected together by an implant channel 30 substantially running through a center of a body 22. In some embodiments, at least one contour of a side 28 may be designed and manufactured to support a desired proposed emergent sulcus profile. According to some embodiments, a bottom 26 of a healing abutment 20 may be configured to fixedly or removably attach to a dental implant.

According to some embodiments, a healing abutment 20 may be selected from a variety of prefabricated healing abutments. A variety of prefabricated healing abutments may be configured to correspond to a collection of data gathered from multiple patients and compiled to generate one or more healing abutments that correspond to certain patient characteristics. For example, in some embodiments a variety of prefabricated healing abutments may be configured to correspond to at least one of a specific tooth shape, a specific tooth size, a specific sulcus shape, a specific sulcus height, a specific concavity shape, a specific concavity depth, and any combination thereof. In some embodiments, a healing abutment may be selected from a variety of prefabricated healing abutments to most closely correspond to a digital model, for example a digital model generated in step 206. According to some embodiments, selection of a healing abutment 20 from a variety of prefabricated healing abutments may lead to reduced costs as a patient-specific abutment does not need to be generated.

In some embodiments, a final abutment may vary from a healing abutment in that it includes additional features such as a post or a chimney to which a crown may be attached (e.g., in the final stages of a surgical procedure). A base of a final abutment may be designed to closely correspond to a healing abutment and a desired emergent sulcus profile (e.g., having corresponding contours), while a chimney of a final abutment may be designed to secure and support a crown in a desired position and orientation relative to an emerged sulcus when the final abutment replaces a healing abutment at a dental implant surgical site.

Figure 3:
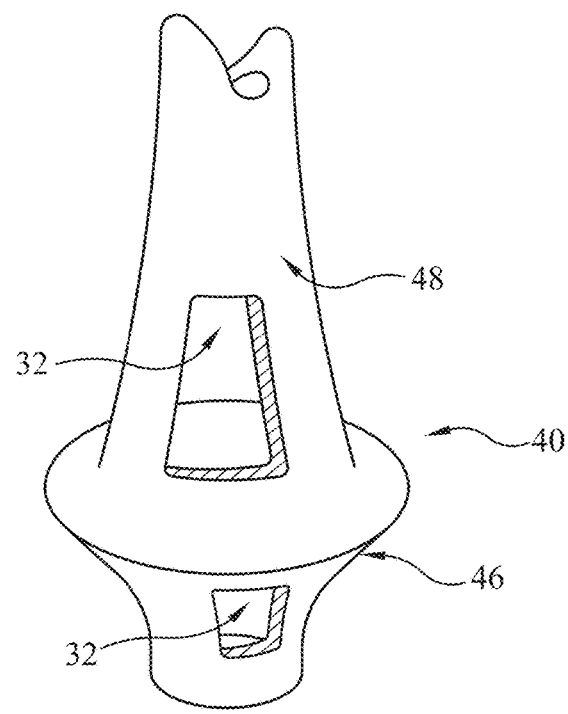
FIG. 3 illustrates a perspective view of a final abutment with a partial cutaway, according to one embodiment of the disclosure.
Figure 4:
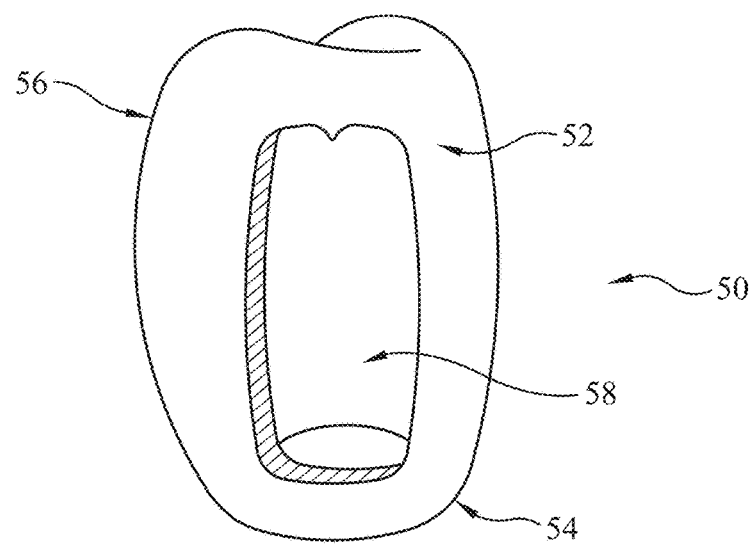
FIG. 4 illustrates a perspective view of a crown with a partial cutaway, according to one embodiment of the disclosure.

In some embodiments, and as substantially shown in FIG. 3, a final abutment 40 may be comprised of a base 46 generally connected to a chimney 48, the base 46 and a chimney 48. In some embodiments a final abutment 40 may be substantially traversed by an implant channel 32 running through a longitudinal center of the final abutment 40. According to some embodiments, a base 46 of a final abutment 40 may be configured to closely match a desired emergent sulcus profile or concavity while a chimney 48 may be configured to orient and hold a crown 50 in a desired position or orientation relative to an emerged sulcus or a soft tissue.

According to some embodiments, a base 46 of a final abutment 40 may be configured to attach (e.g., removably, fixedly) to an implant (e.g., corresponding cross sections, Mohr's taper, screw fastener, glue).

According to some embodiments, a final abutment 40 may be selected from a variety of prefabricated final abutments. A variety of prefabricated final abutments may be configured to correspond to a collection of data gathered from multiple patients and compiled to generate one or more final abutments that correspond to certain patient characteristics. For example, in some embodiments a variety of final abutments may be configured to correspond to at least one of a specific tooth shape, a specific tooth size, a specific sulcus shape, a specific sulcus height, a specific concavity shape, a specific concavity depth, a specific healing abutment, and any combination thereof. In some embodiments, a final abutment 40 may be selected from a variety of prefabricated final abutments to most closely correspond to a digital model generated in step 206. According to some embodiments, selection of a final abutment from a variety of prefabricated final abutments may lead to reduced costs as a patient-specific abutment does not need to be generated.

As illustrated in FIG. 4, a crown 50 may have a crown body 52 including a crown base 54 that is generally connected to a tooth portion 56. In some embodiments, a crown base 54 and a tooth portion 56 may be longitudinally traversed by a chimney channel 58. According to some embodiments, a chimney channel 58 may be configured to receive at least a portion of a chimney 48 of a final abutment 40. A crown base 54 may be configured to include one or more contoured sides configured to substantially align with and sit adjacent to at least one emergent sulcus profile or at least a portion of a concavity (e.g., without stretching or damaging tissue).

As illustrated in FIG. 1, according to some embodiments a method 200 may include creating a digital model of a multiple-piece abutment 206A. Creating a digital model of a multiple-piece abutment 206A may include using a virtual model, a proposed emergent sulcus profile, or both, to create a model of a patient-specific concavity. A patient-specific concavity may be an opening or a tooth socket configured to support an insertion of an implant-abutment combination and a bottom portion of a dental crown and that may be surrounded by an emergent sulcus or soft tissue. According to some embodiments, creating a model of a patient-specific concavity may further include using digital data (e.g., a second data set, a comparison data set) to create a virtual model of a patient-specific multiple-piece abutment. In some embodiments, creating a digital model of a multiple-piece abutment 206A may be followed by manufacturing a multiple-piece abutment 208A.

In some embodiments, a multiple-piece abutment may comprise of a set of abutment caps removably attached to an abutment base that secures to an implant. In some embodiments, a method 200 may include detaching a first abutment cap from an abutment base and attaching a second abutment cap to the abutment base. According to some embodiments, a multi-piece abutment may permit a first abutment cap to be interchanged with a second abutment cap. This "swap out" capability could allow an abutment base to be secured to an implant at a dental implant surgical site and then have direct continuous contact with an emergent sulcus throughout the remainder of a dental implant surgical operation. Such continuous contact may prevent disturbance of one or more fragile, soft-tissue healing processes (e.g., sulcus formation) and thereby reduce the likelihood of tissue damage, tissue discoloration, sulcus retraction, implant failure, or any combination thereof.

According to some embodiments, a multiple-piece abutment that includes an interchangeable abutment cap may eliminate the need for removal and replacement of a temporary healing abutment with a final abutment. In some embodiments, an interchangeable abutment cap may include a healing abutment cap, a flat driver cap, a chimney cap, a temporary crown attachment cap, a dog-leg cap, or any combination thereof.

In some embodiments, an abutment cap may be configured to support a function of a dental implant surgery. For example, according to some embodiments, an abutment cap of a multiple-piece abutment may be configured to include a chimney capable of supporting a crown. In some embodiments, an abutment cap of a multiple-piece abutment may be configured to receive an attachment tool (e.g., a driver wrench), where the attachment tool is capable of driving an implant into a dental surgical site. According to some embodiments, an abutment cap may include a flat driver cap configured to support an emergent sulcus having a desired sulcus profile. A flat driver cap, in some embodiments, may include a cap recess configured to accept an implant driver tip. A flat driver cap may be configured could further have a top that is generally provides a flat top surface. In some embodiments, a multiple-piece abutment may include at least one surface configured to receive a tooth-gap covering device (e.g., at least one substantially flat surface capable of receiving an Essix device, a flipper device, a transitional removable partial denture, or the like).

In some embodiments, one or more sides of an abutment base may be configured to support an emergent sulcus, encourage a desired sulcus profile, or both.

According to some embodiments, an abutment base and an abutment cap may be configured to be removably attached to one another in a manner that permits a rotational force applied to the abutment cap to be transferred to the abutment base and subsequently transferred onto at least one surface of an implant attached to the abutment base.

In some embodiments, a method 200 may include manufacturing a multiple-piece abutment 208A. Manufacturing of a multiple-piece abutment, in some embodiments, may include transferring a dataset generated in 204 (e.g., a virtual model dataset) or a dataset generated in 206A (e.g., a digital model dataset) to a suitable manufacturing means (e.g., a three dimensional printer) which, in some embodiments, may be controlled by a computing means, manufacturing programs, both a computing means and manufacturing programs, or by any other single or combination of controlling means. According to some embodiment, manufacturing a multiple-piece abutment 208A may include processing a dataset generated in 206A to create a patient-specific multiple-piece abutment. For example, manufacturing a multiple-piece abutment 208A may include processing a dataset generated in 206A to create a patient-specific multiple-piece abutment that is modeled and designed to bring about a desired profile of an emergent sulcus or soft tissue development when at least a portion of the multiple-piece abutment is subsequently attached to a dental implant at a dental implant surgical site. According to some embodiments, manufacturing a multiple-piece abutment 208A may include processing a dataset generated in 206A to create a patient-specific multiple-piece abutment that is modeled and designed to complement a concavity.

According to some embodiments, manufacturing a multiple-piece abutment 208A may include generating a set of patient-specific abutment caps with each individual abutment cap being configured to removably attach to an abutment base. In some embodiments, a kit may be formed containing one abutment base and set of abutment caps where the set of abutment caps may include a healing abutment cap, a flat driver cap, a chimney cap, a temporary crown attachment cap, a dog-leg cap, or any combination thereof.

According to some embodiments, a set of abutment caps may be selected from a variety of prefabricated abutment sets. A variety of prefabricated abutment sets may be configured to correspond to a collection of data gathered from multiple patients and compiled to generate one or more abutment sets that correspond to certain patient characteristics. For example, in some embodiments a variety of abutment cap sets may be configured to correspond to at least one of a specific tooth shape, a specific tooth size, a specific sulcus shape, a specific sulcus height, a specific concavity shape, a specific concavity depth, a specific healing abutment, and any combination thereof. In some embodiments, a prefabricated abutment set may be selected from a variety of prefabricated abutment sets to most closely correspond to a digital model generated in step 206A. According to some embodiments, selection of an abutment set from a variety of prefabricated abutment sets may lead to reduced costs as such selection reduces the number of patient-specific abutments that need to be generated.

A method 200, in some embodiments, may further include creating a crown 210A. Creating a crown 210A, according to some embodiments, may include transmitting one or more datasets (e.g., a virtual model dataset from step 204, a digital model dataset from step 206A) to a computing/manufacture means and processing the one or more datasets to create a crown.

As illustrated in FIG. 4, a crown 50 may have a crown body 52 including a crown base 54 that is generally connected to a tooth portion 56. In some embodiments, a crown base 54 and a tooth portion 56 may be longitudinally traversed by a chimney channel 58. According to some embodiments, a chimney channel 58 may be configured to receive at least a portion of a chimney 48 of a final abutment 40. A crown base 54 may be configured to include one or more contoured sides configured to substantially align with and sit adjacent to at least one emergent sulcus profile or at least a portion of a concavity (e.g., without stretching or damaging tissue). In some embodiments, a crown base 54 may include one or more contours (e.g., at the location where the crown base intersects an emergent sulcus) configured to substantially align with one or more of an emergent sulcus profile, a concavity, and a base top.

According to some embodiments, a method 200 may further include applying a multiple-piece abutment to a dental implant site 212A. In some embodiments, applying a multiple-piece abutment to a dental implant site may include inserting an implant. Inserting an implant may include attaching a tip of an implant driver to an implant to generate an implant-driver combination, and driving the implant into a dental implant surgical site. Driving an implant into a dental implant surgical site may include rotating an implant driver such that an implant driver-implant combination is rotated within a dental surgical site and thereby screws in or otherwise embeds the implant portion of the driver-implant combination into the dental implant surgical site.

Figure 7:
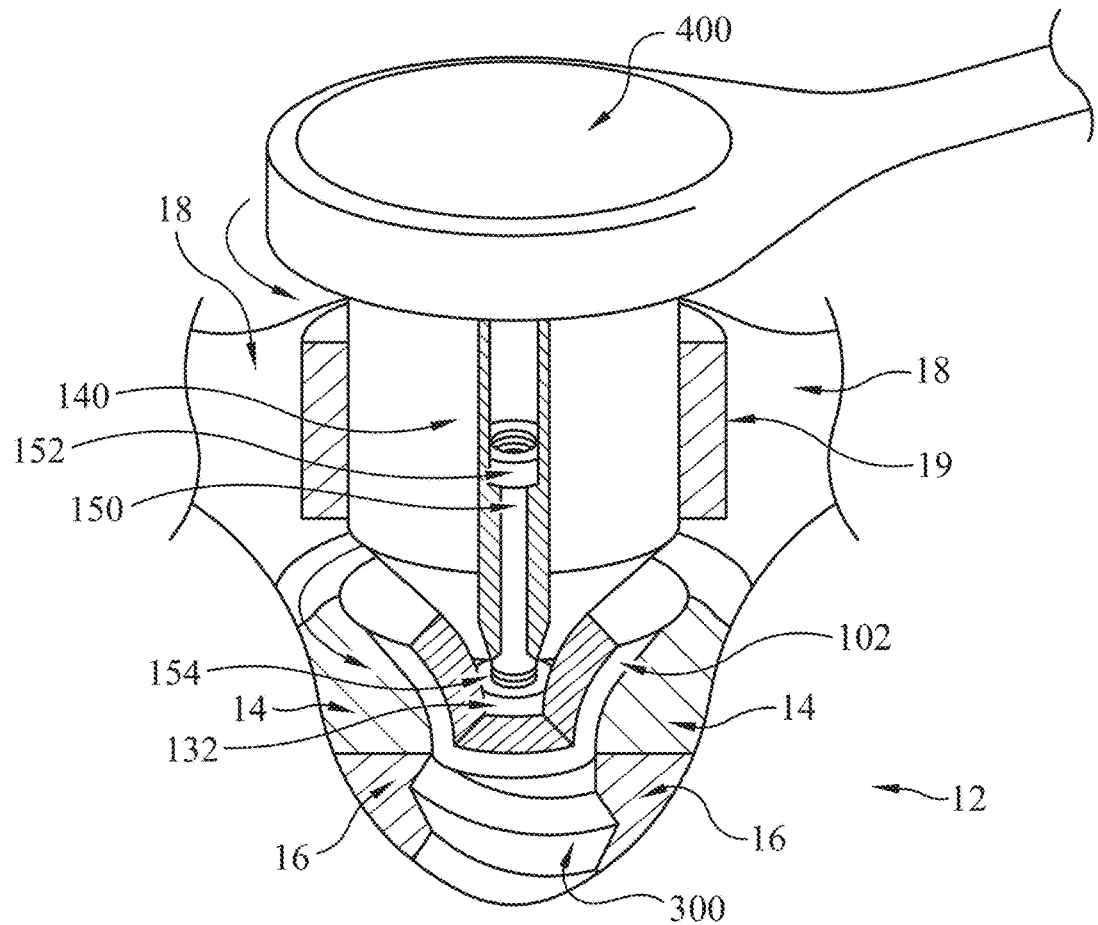
FIG. 7 illustrates a perspective cutaway view of a cap configured to secure an abutment-implant combination into a dental implant site, according to one embodiment of the disclosure.
Figure 8:
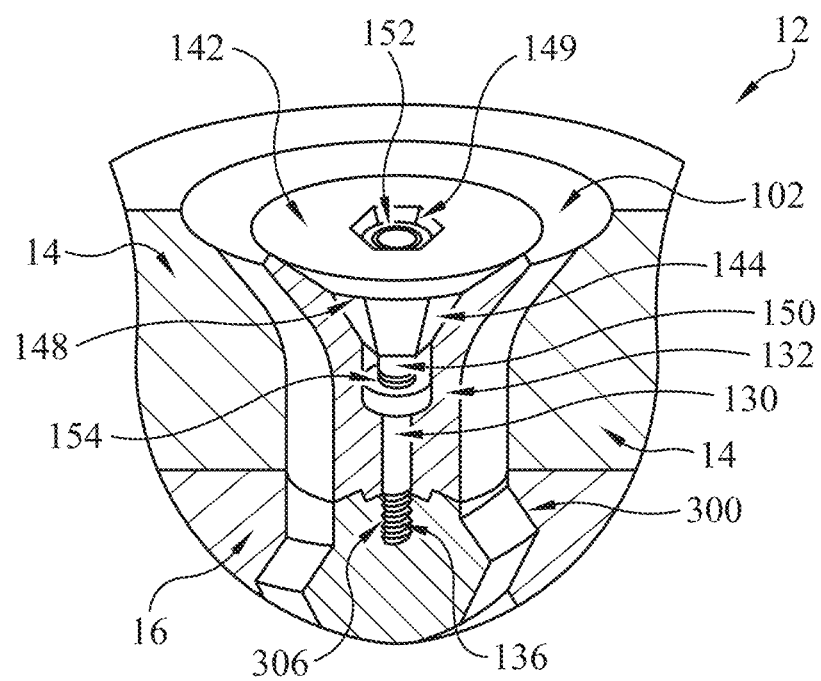
FIG. 8 illustrates a perspective cutaway of a cap-abutment-implant combination configured to conserve space, according to one embodiment of the disclosure.

As illustrated in FIG. 7, according to some embodiments, an implant driver-implant combination may be configured to be driven through a guide barrel 19 of a dental implant surgical guide 18. A dental implant surgical guide 18 may be placed over a dental implant surgical site 12 such that a guide barrel 19 aligns with an implant site (e.g., an angle of trajectory) such that an implant may be driven through the guide channel by the implant driver in such a way that the implant is correctly positioned, oriented, or otherwise placed into the dental implant surgical guide. In some embodiments, both a driver and an implant driver-implant combination may be configured to move through a guide barrel of a dental implant surgical guide 18 placed over a dental implant surgical site. In some embodiments, an implant driver may be released from an implant once the implant is properly secured to a dental implant surgical site, and the release of the implant driver from the implant may allow the subsequent attachment of a multiple-piece abutment to the implant.

In some embodiments, an abutment base may be applied to an implant prior to the implant being secured to a dental implant surgical site. According to some embodiments, an implant driver may be secured to an abutment base 112 (e.g., a base receptacle) such that the implant driver is incapable of rotating within the abutment base and generating an implant-driver-abutment base combination. For example, in some embodiments, an implant driver-abutment base combination may be formed by securing a tip of an implant driver in a base receptacle of an abutment base and thereby prevent stripping of the base receptacle (e.g., stripping of one or more threads of a base receptacle) or breaking the fastener from the abutment base, by preventing rotation of the tip within the base receptacle. An implant driver-abutment base combination may be rotated, in some embodiments, such that an implant is rotated through a guide barrel 19 of an implant surgical guide 18 and inserted into a dental surgical site. According to some embodiments, an implant driver-abutment base combination may then be disassembled by detaching the implant driver. In some embodiments, after detaching an implant driver from an implant driver-abutment base combination, an abutment cap (e.g., a healing abutment cap) may be removably attached to the abutment base.

In some embodiment, a multiple-piece abutment (e.g., having at least an abutment base and an abutment cap) may be attached to an implant prior to the implant being secured into a dental implant surgical site. According to some embodiments, an abutment base may be attached to an implant, and a selected abutment cap (e.g., a driver cap) may be removably attached to the abutment base. An abutment cap, in some embodiments, may be configured with a tall, cylindrical side capable of removably engaging an inner side of a guide barrel 19 of a dental surgical guide 18. According to some embodiments, an abutment cap of a multiple-piece abutment may further include a chimney configured to receive a final prosthesis (e.g., a crown). In some embodiments, an implant, an abutment base, and an abutment cap may be attached and inserted through a guide barrel of a dental surgical guide to allow the implant to engage a dental implant surgical site in a manner that allows increased control of a depth, a trajectory, a rotation, or any combination thereof. In some embodiments, an abutment cap may be configured such that a side of the abutment cap aligns with a guide cylinder of a surgical guide and may be configured to guide a combination of an implant, an abutment base, and the abutment cap through the guide cylinder in a manner that allows the implant to be inserted into the surgical site at a desired orientation, position, location, and depth. After an implant has been properly secured into the dental surgical site, an implant driver (e.g., a driver wrench) may be removed from an abutment cap, according to some embodiments, and an abutment cap (e.g., a driver cap) may be detached and replaced with another abutment cap (e.g., a healing cap) that could function to further assist with additional stages of a dental implant surgery. According to some embodiments, after insertion of an implant into a surgical implant site and removal of a an implant driver, a gum tissue may be sutured to remove any gaps between an abutment base and a sulcus.

According to some embodiments, an abutment cap may comprise a flat driver cap configured to receive a tip of an implant driver. An implant tip driver, in some embodiments, may be used to attach a flat driver cap to an abutment base.

In some embodiments, after insertion of an implant into a surgical implant site, an implant tip driver may be removed leaving a flat driver cap attached to an abutment base and the abutment base attached to the implant. According to some embodiments, a temporary retainer (e.g., an Essix type, a temporary crown) may be secured over a flat driver cap, according to some embodiments, as a top surface of the flat driver cap may be configured to receive a bottom of a temporary retainer or a temporary crown. A temporary retainer or a temporary crown may allow a patient to have normal mouth movement and use while a sulcus heals and grows at a surgical site. Additionally, a temporary retainer or temporary crown may protect an implant (e.g., from forces that would interfere with osseointegration).

Healing of a dental surgical site and growth of an emergent sulcus is important for the successful implantation of a prosthesis. Because an implant is inserted into bone tissue, sufficient time is required for osseointegration before significant pressure is applied to the implant. Moreover, generation of an emergent sulcus with a desired profile contributes to a desirable overall appearance at a dental implant site. Damage to tissue in and around an emergent sulcus can lead to retraction of the sulcus or discoloration of tissue, thereby leading to a less desirable appearance. According to some embodiments, a method 200 may include affixing a crown 214A. Affixing a crown 214A, in some embodiments, may include removing a temporary retainer or a temporary crown after sufficient healing and development of an emergent sulcus has taken place, and inserting a chimney cap top. According to some embodiments, affixing a crown 214A may include removal (e.g., with the use of a laser or a scalpel) of any tissue overgrowth on an abutment cap (e.g., a thin, healthy keratinized tissue overgrowth formed over a cap top). According to some embodiments, affixing a crown 214A may include unfastening and removing an abutment cap (e.g., a flat driver cap, a healing abutment cap) from an abutment base.

In some embodiments, affixing a crown 214A may include attaching an abutment cap (e.g., a chimney-top cap, a dog-leg cap). In some embodiments, an abutment cap may be a chimney-top cap configured with a chimney capable of supporting a crown. According to some embodiments, affixing a crown 214A may include affixing a dog-leg cap configured with an angular structure and capable of supporting a crown, a chimney-top cap, or both. In some embodiments, a dog-leg cap may be configured to have both an angular structure and a chimney capable of supporting a crown. A dog-leg cap may be configured to allow a crown or a temporary crown to be oriented at a desired angle in situations where an implant is oriented at an alternative angle. For example, in some embodiments a patient's bone structure may not support an implant at an angle suitable for the trajectory of a crown; thus, an implant may be inserted at an alternative angle that the patient's bone structure will support and after osseointegration a dog-leg cap may be attached to an abutment base and a crown or a temporary crown may be attached to the dog-leg cap, with the dog-leg cap having an angle that places the crown or the temporary crown in a desirable alignment with the patient's jaw and other teeth.

In some embodiments, affixing a crown 214A may further include affixing (e.g., removably, permanently) a crown to an abutment cap (e.g., a chimney-top cap, a dog-leg cap). For example, in some embodiments, a method 200 may include permanently affixing (e.g., appropriately cemented or otherwise affixed) a crown to a chimney of a chimney-top cap. In some embodiments an abutment base may continue to provide to support an emergent sulcus during step 214A and after crown attachment. According to some embodiments, after affixing a crown 214A, a method 200 may proceed at another dental implant site with gathering patient data 202 or creating a virtual model 204.

Figure 5:
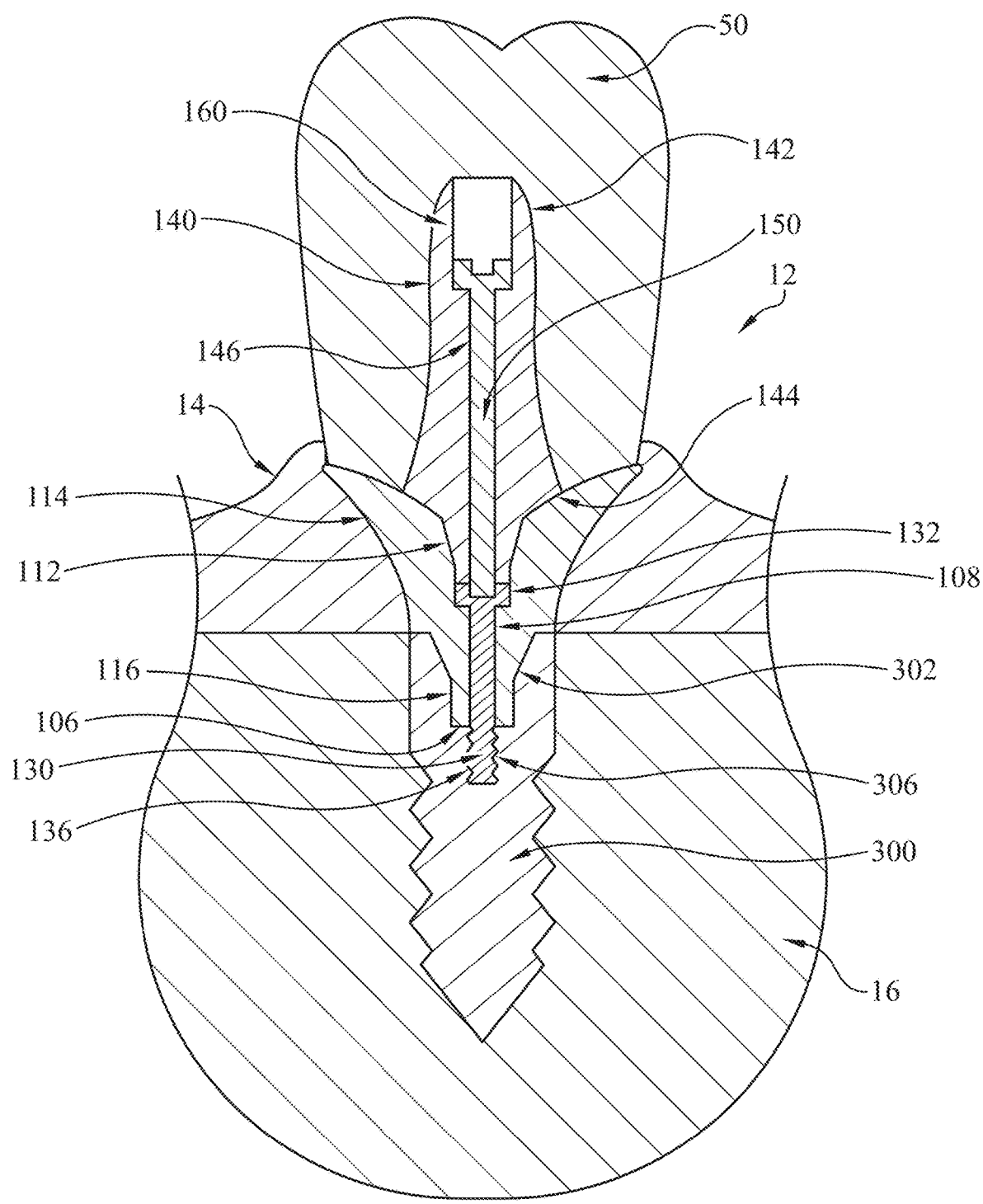
FIG. 5 illustrates an elevation cutaway view of a multiple-piece abutment, according to one embodiment of the disclosure.
Figure 6:
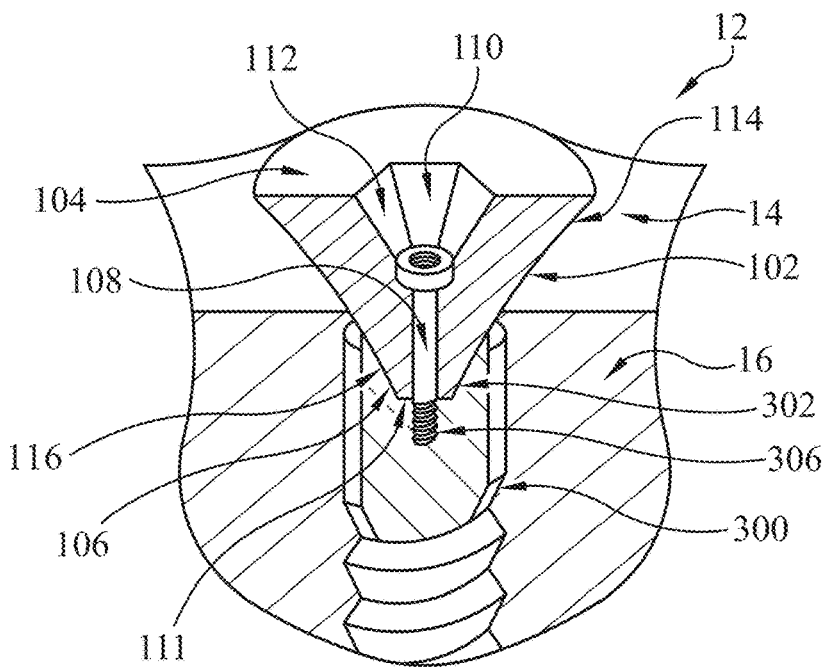
FIG. 6 illustrates a perspective cutaway view of an abutment base, according to one embodiment of the invention.

As substantially shown in FIGS. 5, 6, 7, 8 and 9 some embodiments of the present disclosure include a multiple-piece abutment configured to encourage and support a desired emergent sulcus profile. In some embodiments, a multiple-piece abutment may be designed and manufactured using a method 200. As illustrated in FIGS. 5 and 6, a multiple-piece abutment may attach to an implant 300 at a surgical site 12. An implant 300 may be inserted into a prepared bone 16 at a surgical site 12 and, in some embodiments, may include a top cup 302 configured to receive a first portion of a multi-piece abutment (e.g., an abutment base) and an implant receptacle 306 configured to receive a second portion of the multi-piece abutment (e.g., a threaded portion of a base fastener). An implant receptacle 306 may be threaded to receive a threaded portion of a multiple-piece abutment (e.g., a threaded portion of a base fastener) and thereby removably attach a multiple-piece abutment to an implant 300, according to some embodiments.

A multiple-piece abutment, in some embodiments, may include an abutment base 102 and an abutment cap 140 (e.g., selected from a set of abutment caps). According to some embodiments, an abutment base 102 may be configured to removably attach to an implant 300 and to substantially encourage the development and support of an emergent sulcus 14. In some embodiments, an abutment base 102 may be patient-specific, digitally designed, and manufactured to encourage the development and support of an emergent sulcus 14 with a patient-specific profile. An abutment base 102 may be configured, in some embodiments, to receive a bottom portion of a crown 50 (e.g., a patient specific crown).

In some embodiments, an abutment base 102 may be selected from a variety of prefabricated abutment bases. A variety of prefabricated abutment bases may be configured to correspond to a collection of data gathered from multiple patients and compiled to generate one or more abutment bases that correspond to certain patient characteristics. For example, in some embodiments a variety of abutment bases may be configured to correspond to at least one of a specific tooth shape, a specific tooth size, a specific sulcus shape, a specific sulcus height, a specific concavity shape, a specific concavity depth, a specific healing abutment, and any combination thereof. According to some embodiments, an abutment base may be composed of at least one biocompatible material (e.g., pekton, peek, gold, titanium, composites).

In some embodiments, an abutment base 102 may be configured to attach to an implant 300 at a dental implant surgical site 12 and provide support for an emergent sulcus profile (e.g., as provided by a base side). According to some embodiments, an abutment base 102 is configured to configured to remain attached to an implant at a dental surgical site 12 and thereby allowing the emergent sulcus to engage with a profile of the abutment base and secure to an exposed bone portion of the dental surgical site. According to some embodiments, an abutment base 102 may remain secured to an implant throughout a remainder of a dental surgical procedure (e.g., an emergent sulcus remains in contact with the abutment base during osseointegration), after a final crown 50 is secured, or permanently.

As illustrated in FIGS. 5 and 6, in some embodiments, an abutment base 102 may include a base top 104 and a base bottom 106 generally connected by a continuous side 114. According to some embodiments, an abutment base 102 may be configured such that a continuous side 114 encourages and supports a desired emergent sulcus profile (e.g., contour). In some embodiments, a base top 104 may include a scalloped region such that one or more edges of the scalloped region align with the desired emergent sulcus profile.

According to some embodiments, an abutment base 102 may be configured to include a base projection 116 that substantially aligns with and at least a portion of and fits within a top cup 302 of an implant 300, as illustrated in FIG. 6. In some embodiments, one or more projection sides delineating a base projection 116 may be configured angularly and may correspond to one or more sides of a top cup 302 of an implant 300. According to some embodiments, an abutment base 102 may be configured to connect to an implant 300 by placing a bottom base projection 116 within the implant top cup 302. Accordingly, in some embodiments an abutment base 102 may be configured with a base projection 116 that complements an implant top cup 302 (e.g., having complementary angled sides) such that the abutment base is substantially prevented from rotating (e.g., around the base fastener 130 and within the implant top cup 302) relative to the implant 300. In some embodiments, an abutment base 102 may be configured to transfer rotational or torsional force to an implant 300 that is part of an implant-abutment combination thereby contributing to an attachment of a dental implant 300 to a dental implant surgical site 12. In some embodiments, an abutment base 102 attached to an implant 300 (e.g., prior to the attachment of the dental implant 300 to the dental implant surgical site 12) may transfer a rotational force placed upon the abutment base and further drive the abutment-implant combination into the dental implant surgical site 12. According to some embodiments, an abutment base 102 may be attached to the dental implant 300 after the dental implant 300 has been attached to the dental implant surgical site 12 (e.g., using an implant driver attached directly to the implant). In either case, an abutment-implant combination configured such that a base projection of an abutment base is complementary to a top cup of an implant may generate a locking mechanism capable of preventing a rotation of the abutment base 102 relative to the implant 300 (and the base projection 116 from rotating within the abutment base 102). In some embodiments such a locking mechanism may permit maintenance of a proper orientation (e.g., telemetry) of an abutment base 102 relative to a dental implant surgical site 12, an emergent sulcus 14, a crown 50, or any combination thereof.

In some embodiments, a base top 104 and a base bottom 106 may be continuously connected through a centerline double-open-ended base channel 108 that is configured to accommodate a base fastener 130 configured to attach (e.g., removably) the abutment base 102 to an implant 300, in some embodiments. A centerline double-open-ended base channel 108, in some embodiments, may be configured to have a first channel end 110 located proximate to a base top 104 and a second channel end 111 located proximate to a base bottom 106. According to some embodiments, a first channel end 110 may be configured to form a base receptacle 112, as illustrated in FIG. 6. A base receptacle 112 may be configured to receive a base fastener and to secure a base fastener head 132. A base fastener head 132 may be configured to be secured within a double-open ended base channel 108 and may have any shape that permits such a secure seat including, for example, a hex head, a pyramid head, a flat head, a washer head, a hexagon-washer head, and a clock head. In some embodiments, a base receptacle 112 and a base fastener 132 may be configured such that when inserted and secured into the base receptacle, the base fastener is secured at a level below that of a base top 104. In some embodiments, a base receptacle 112 may be configured to receive and removably secure a tip of an implant driver.

According to some embodiments, a bottom edge of a base fastener 130 may be configured to traverse an entire length of a double open-ended base channel 108 and to penetrate a base bottom 106 and extend into an implant threaded receptacle 306 of an implant 300.

Figure 9:
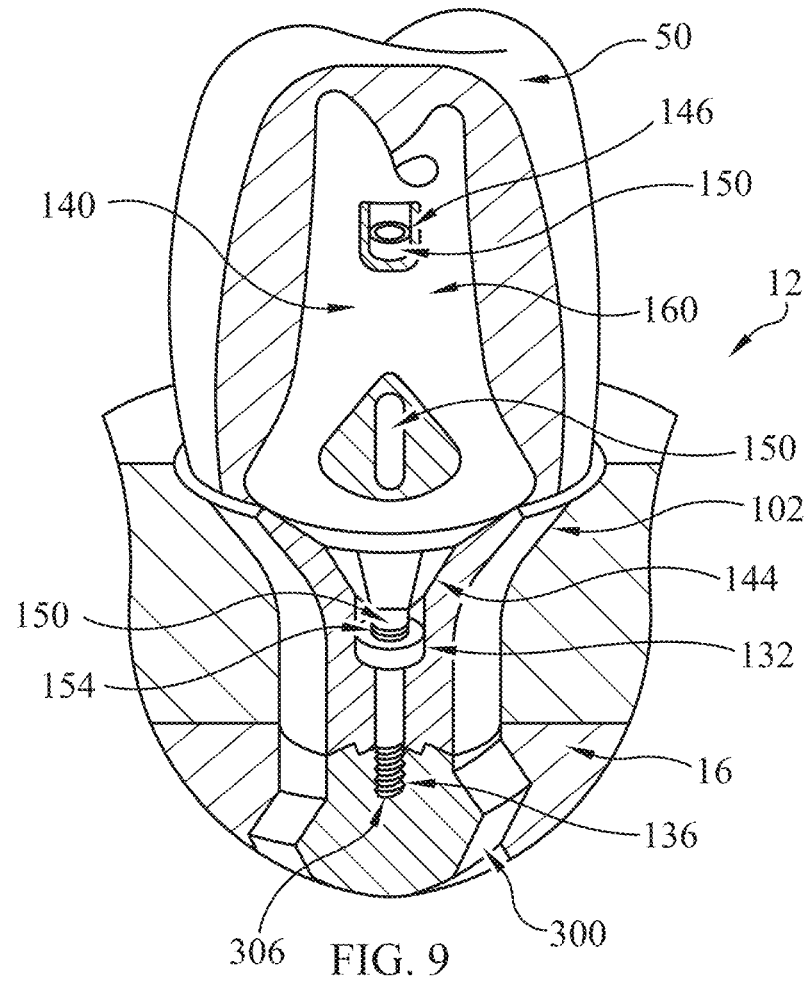
FIG. 9 illustrates a perspective cutaway of a crown-supporting combination of a cap, multi-piece abutment, crown, and implant combination, according to one embodiment of the disclosure.

According to some embodiments, a multiple-piece abutment may further include one or more abutment caps. In some embodiments, an abutment cap 140 may not contact or otherwise directly interface with the emergent sulcus 14 at the dental implant surgical site 12 (e.g., FIG. 9 illustrating a chimney cap completely encompassed by a crown). According to some embodiments, at least a portion of an abutment cap 140 (e.g., a flat driver cap, a healing abutment) may contact or directly interface with an emergent sulcus 14 at a dental implant surgical site 12.

According to some embodiments, an abutment cap 140 may serve a specific function in a dental implant surgery. For example, in some embodiments, an abutment cap 140 may function as an implant driver (e.g., a driver cap); as a protective covering over a dental implant surgical site as defined by the teeth on each side of the dental implant surgical site (e.g., a temporary crown); or as an attachment support for a crown (e.g., a chimney cap). An abutment cap 140, in some embodiments, may include a healing abutment cap, a flat driver cap, a chimney cap, a temporary crown attachment cap, a dog-leg cap, or any combination thereof. According to some embodiments, a multiple-piece abutment may include a set of abutment caps, with each of the set of abutment caps being configured to fulfill a distinct function within a dental implant surgical procedure. In some embodiments, a multiple-piece abutment may be configured to permit removable attachment of an abutment cap 140 to an abutment base 102 thereby allowing a first abutment cap (e.g., a driver cap) to be exchanged for a second abutment cap (e.g., a healing abutment, a dog-leg abutment) once the first abutment cap's respective function is completed.

According to some embodiments, an abutment cap 140 may include a cap fastener 150 configured to attach (e.g., removably) the abutment cap to an abutment base 102. A cap fastener, in some embodiments, may be configured to attach (e.g., removably) to a base fastener. In some embodiments, an abutment cap 140 may include a cap channel 146 configured to allow a cap fastener 150 to pass through the abutment cap and attach to a base fastener 130. In some embodiments, a cap channel 146 may include a double-open-ended channel traversing a centerline of an abutment cap 140. A cap channel 146, in some embodiments, may be configured to have a first cap channel end located at or near a proximate end of a channel cap and a second cap channel end located proximate to a base fastener 130. In some embodiments, a base fastener 130 may be configured to complement and attach to (e.g., removably) a cap fastener 150. A cap fastener 150, according to some embodiments, may be configured to complement and attach to (e.g., removably) a base fastener 130. In some embodiments a cap fastener 150 may be configured to complement a configuration of a base fastener head 132. For example, in some embodiments, a cap fastener 150 may be configured to complement a base fastener head 132 having a hex head shape, a pyramid head shape, a flat head shape, a washer head shape, a hexagon-washer head shape, or a clock head shape. According to some embodiments, a cap fastener 150 may include a threaded portion. A threaded portion of a cap fastener 150 may include an entire length of the cap fastener or any portion thereof. In some embodiments, a threaded portion of a cap fastener may be configured to allow a threaded portion of a base fastener 136 to receive (e.g., removably) at least a portion of the threaded portion of the cap fastener.

According to some embodiments, a cap fastener may include a cap fastener head 152. A cap fastener head 152 may be configured as any suitable shape, including for example: a hex head, a pyramid head, a flat head, a washer head, a hexagon-washer head, or a clock head.

In some embodiments, an abutment cap 140 may include a cap bottom 144 and a cap top 142. A cap bottom 144, according to some embodiments, may have a generally hemispherical shape configured to complement a base top 104 (e.g., a scalloped shape) of an abutment base 102. A cap bottom projection may include a second cap channel end, in some embodiments. In some embodiments, a cap bottom 144 may include a cap bottom projection configured to complement a base receptacle 112 of an abutment base 102. According to some embodiments, a cap bottom projection may be configured to complement a base receptacle 112 such that the cap bottom projection may be removably received within the base receptacle in a manner that prevents the cap bottom projection from rotating within the base receptacle (e.g., angled walls of cap bottom projection may fit against corresponding angled walls of the base receptacle). A complementary fit between a cap bottom projection and a base receptacle may, in some embodiments, permit a multiple-piece abutment to be rotated as a single unit with limited friction or undesirable forces between individual components of the multiple-piece abutment. In this manner, a rotational or torsional force as substantially applied to an abutment cap component of a multiple-piece abutment may be directly transmitted to an abutment base component and thereby apply the rotational or torsional force onto a dental implant, allowing the dental implant to rotate and anchor within a dental implant surgical site 12. Such complementary attachment between an abutment cap and an abutment base, as well as, an attachment between an abutment base and an implant may, in some embodiments, prevent rotational force(s) exerted upon the abutment cap from being transferred through a cap fastener, a base fastener, or both and thereby weakening or breaking these elements (e.g., as a result of torsional or rotational strain).

A multiple-piece abutment combination attachment capability (e.g., cap fastener-base fastener combination) may be desirable for anchoring an implant 300 to a dental implant surgical site or to an analogue dental implant site of a model of the patient's mouth. Other removable means of attachment could be substituted for holding the cap fastener-base fastener combination/implant to generally secure together the multiple-piece abutment-implant combination and still be considered to be under the purview of the present disclosure.

An abutment cap 140 may be configured to function for a particular purpose (e.g., supporting a cap) during a dental implant surgery or as a permanent structure. As substantially shown in FIG. 8, an abutment cap 140, in some embodiments, may be configured as a flat driver cap. A flat driver cap may be configured to maintain a proper spacing between one or more teeth that are adjacent to a dental implant surgical site, according to some embodiments. In some embodiments, a flat driver cap may be configured to protect a dental surgical site from undesirable disturbances or objects (e.g., to prevent a patient from inserting their tongue into a gap formed by the dental implant surgical site resulting in possible undesirable disturbance of implant, dental implant surgical site, or both). According to some embodiments, a cap top 142 of a flat driver cap may have a generally flat or planar appearance or may have a slight semispherical rise. In some embodiments, a cap top 142 of a flat driver cap may include a cap recession 149 configured as a first cap channel end of a cap channel. In some embodiments, a cap recession 149 may be configured to receive a tip of an implant driver in such a manner so that the tip does not rotate within the cap recession. According to some embodiments, a cap recession 149 may be configured to accommodate a cap fastener head 152 of a cap fastener. In some embodiments, a cap fastener 150 may include a threaded portion 154 configured to attach (e.g., removably) to a base fastener head 132.

According to some embodiments, a temporary crown device (e.g., Temporary Fixed Partial Denture, Maryland Bridge, Snap on Smile, Essix Retainer, Flipper (Acrylic Removable Partial Denture) may be fitted over a dental surgical site having a multiple-piece abutment including a flat driver cap. A temporary crown device may rely upon a suitable anchoring system that removably attaches the temporary crown device to teeth neighboring the dental implant surgical site to project a covering or provisional tooth or crown into the gap and over the abutment to keep the patient from (generally unconsciously) from disturbing the placed implant or dental implant surgical site until the dental implant surgical site has healed to firmly secure the implant in place through osseointegration.

After the dental implant surgical site 12 has substantially healed and proper osseointegration has generally occurred to secure the implant 300 along with a healing proper emergent sulcus profile, any placed tooth gap preserving device (e.g., Essix) could be removed to again allow access to the abutment cap 140. A cap fastener 150 could be disengaged from a base fastener 130 and an abutment cap configured as a flat driver cap and replaced with an alternative abutment cap (e.g., a chimney cap).

As substantially shown in FIG. 7, another variation of an abutment cap 140 may be configured as a cylindrical driver cap. In some embodiments, a cylindrical driver cap may be configured with a substantially cylindrical shape capable of moveably engaging a guide barrel 19 of a dental implant surgical guide 18. According to some embodiments, engaging a guide barrel 19 of a dental implant surgical guide 18 may permit more precise guidance of a placement of an implant 300 into a dental implant surgical site 12 (e.g., enhanced control of a trajectory or a depth of placement of the implant). In some embodiments, a cylindrical driver cap may have an extended cylindrical shape allowing greater contact area between a guide barrel 19 of a dental implant surgical guide 18 and the cylindrical driver cap compared to an abutment cap having less contact area with the guide barrel. Such increased contact area may allow greater control and precision of inserting an implant at a dental surgical site (e.g., implant positioning, telemetry and orientation). Once the implant portion of an implant-multiple-piece abutment combination is properly attached to a prepared bone 16 at the dental implant surgical site 12, in some embodiments, an abutment cap 140 configured as a cylindrical driver cap may be removed from an abutment base and replaced with an alternative abutment cap such as a flat driver cap.

In some embodiments, an abutment cap 140 configured as a cylindrical driver cap may include a cap channel configured to accommodate a cap fastener having a cap fastener head 152 and a threaded portion 154. In some embodiments, a cap fastener 150 may include a threaded portion 154 configured to attach (e.g., removably) to a base fastener head 132. An abutment cap 140 configured as a cylindrical driver cap may be configured to removably attach to a driver wrench 400 or another driving tool capable of rotating an implant-multiple-piece abutment combination to affix the implant 300 to a dental implant surgical site 12.

According to some embodiments, an abutment cap 150 may be configured as a chimney cap configured to support a crown, as illustrated in FIGS. 5 and 9. In some embodiments, an abutment cap 140 configured as a chimney cap may include a vertically-oriented chimney 160 configured to be received by a chimney channel (e.g., 58 of FIG. 4) of a crown (e.g., 50 of FIG. 4). According to some embodiments, a crown 50 may be affixed (e.g., by acrylic glue) to a chimney 160 to hold the crown 50 in place upon an implant-multiple-piece abutment combination.

As illustrated in FIG. 9, in some embodiments an abutment cap 140 may be configured as a chimney cap and may include a cap channel 146 configured to accommodate a cap fastener 150 having a threaded portion 154. In some embodiments, a cap fastener 150 may include a threaded portion 154 configured to attach (e.g., removably) to a base fastener head 132. An abutment cap 140 configured as a cylindrical driver cap may be configured to removably attach to a driver wrench 400 or another driving tool capable of rotating an implant-multiple-piece abutment combination to affix the implant 300 to a dental implant surgical site 12.

In one embodiment, a cap channel 146 for both a chimney cap and a cylinder driver cap could be stepped to form a shelf upon which an edge of a hex head of a cap fastener could rest when securing the chimney cap or the driver cap to the abutment base. In that manner, a cap fastener 150 with the same length could be used on all extended height caps (e.g., cylinder driving cap, chimney cap, etc.) as well as lower height caps (e.g., flat driver cap).

According to some embodiments, an abutment cap 140 configured as a cap bottom 144 and a cap top where the cap top is a chimney 160 may be configured as a single piece or as separate pieces. In some embodiments where an abutment cap 140 is configured as a cap bottom 144 and a chimney 160 as separate pieces, the pieces may be configured such that a double-open-ended channel traverses both pieces and a cap fastener may be configured to connect the separate pieces and attach to a base fastener head.

According to some embodiments, a crown and a chimney may be configured as a single piece (e.g., fused, manufactured as a single piece). In some embodiments, a crown-chimney single piece may be configured to affix to an abutment base.

In some embodiments a chimney may be angled. An angled chimney may permit attachment of a chimney to a surgical site oriented in an angular or non-vertical orientation. In some embodiments, for example when a patient has limited suitable bone tissue for insertion of an implant, an implant and abutment base may be oriented at an angle inappropriate for attachment of a crown in a line directly aligning with the implant, in such scenarios an angled chimney cap (e.g., angled such that the chimney aligns with an intended placement of a crown) may be attached to an abutment base and a crown attached to the chimney cap. A chimney portion of a chimney cap may have any angle.

In some circumstances a patient may insufficient or inappropriate bone density to insert an implant in a substantially vertical direction (i.e., substantially perpendicular to the patient's gum line). The present disclosure further relates to a multiple-piece abutment configured to facilitate insertion of an implant-multiple-piece abutment-crown combination in circumstances where an implant must be inserted in an angular or non-vertical orientation relative to a patient's gum line (e.g., due to insufficient bone density or structure).

Figure 10:
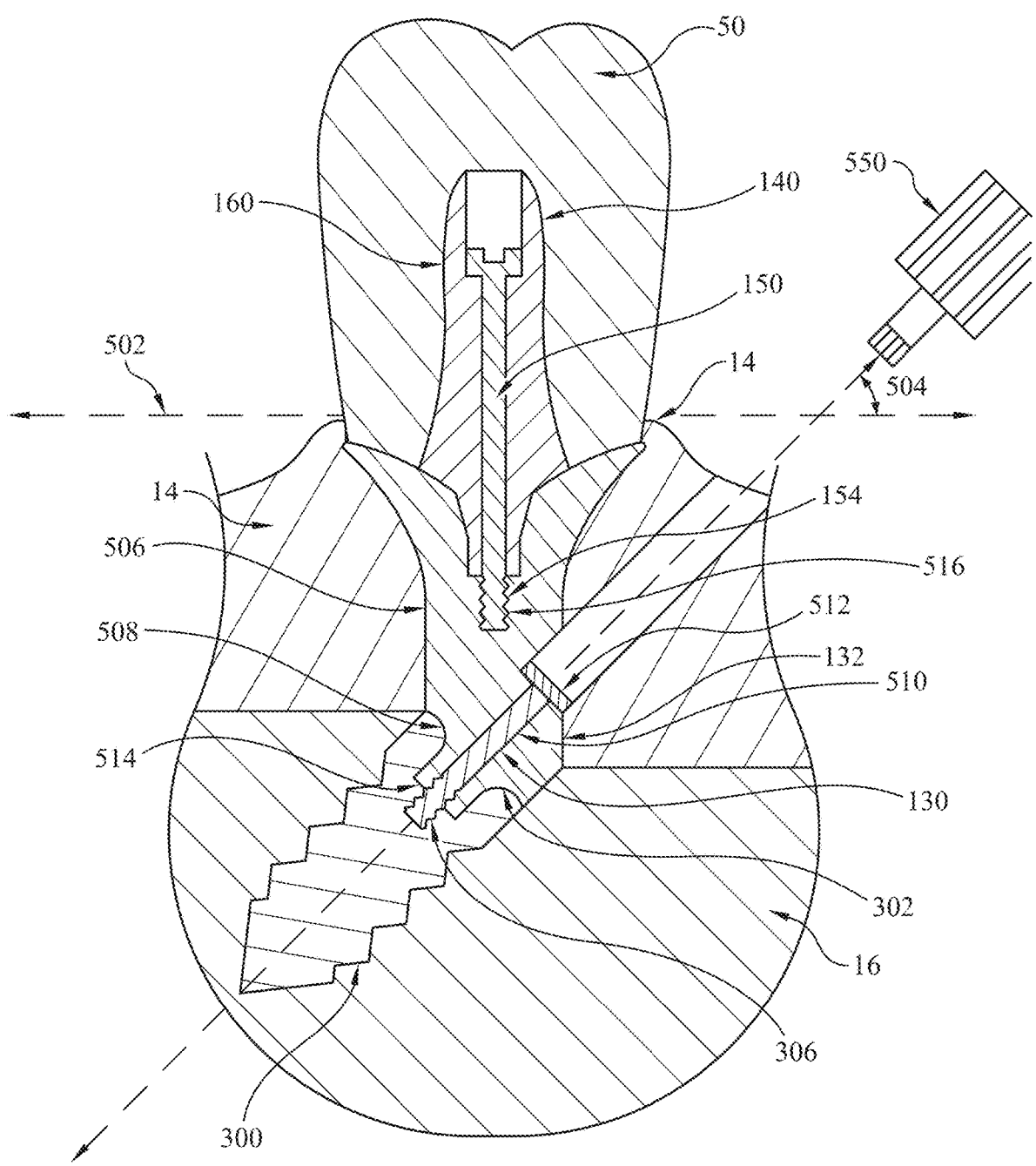
FIG. 10 illustrates an implant-multiple-piece abutment-crown combination in circumstances where an implant must be inserted in an angular or non-vertical orientation relative to a patient's gum line, according to one embodiment of the disclosure.

As illustrated in FIG. 10, in some embodiments an implant 300 may be inserted in a prepared bone 16 at an angle 504 relative to a line substantially perpendicular to a patient's gum line 502. The angle 504 can be adjusted to suit the patient's anatomy to find the most secure placement of the implant 300 within the bone tissue 16, so that the threads of the implant 300 can secure sufficient purchase against the bone 16 and maximize osseointegration of the implant 300 into the bone 16. The angle 504 can range between a few degrees to as many as 45 degrees, but preferably less then about 30 degrees. An implant 300 may be inserted into a prepared bone 16 at a surgical site 12 and, in some embodiments, may include a top cup 302 configured to receive a first portion of a multi-piece abutment (e.g., an abutment base) and an implant receptacle 306 configured to receive a second portion of the multi-piece abutment (e.g., a threaded portion of a base fastener). An implant receptacle 306 may be threaded to receive a threaded portion of a multiple-piece abutment (e.g., a threaded portion of a base fastener) and thereby attach a multiple-piece abutment to an implant 300, according to some embodiments.

According to some embodiments, and as illustrated in FIG. 10, a dog-leg multiple-piece abutment including an abutment base and an abutment cap may be configured to compensate for an insertion of an implant at an angle such that a crown may be inserted in a line substantially perpendicular to a patient's gum line and an emergent sulcus may be formed with a desired profile (e.g., a dog-leg configuration). According to some embodiments a dog-leg multi-piece abutment may be configured to have an angled abutment base, an angled abutment cap, or both.

As illustrated in FIG. 10, a dog-leg multiple-piece abutment may include an angled abutment base 506 configured to include an angled base projection 508 that substantially aligns with and at least a portion of fits within a top cup 302 of an implant 300. According to some embodiments, an angled abutment base 506 may be configured to connect to an implant 300 by placing an angled base projection 508 within the implant top cup 302. Accordingly, in some embodiments an angled abutment base 506 may be configured with an angled base projection 508 that complements an implant top cup 302 (e.g., having complementary angled sides) such that the abutment base is substantially prevented from rotating relative to the implant 300.

In some embodiments an angled abutment base 506 may include a double-open-ended angled base channel 510 that is configured to accommodate a base fastener 130 configured to attach (e.g., removably) the angled abutment base 506 to an implant 300, in some embodiments. An angled base channel 510, in some embodiments, may be configured to have a first end 512 located along a side of the angled base channel at an angle 504 corresponding to the angle of insertion of implant 300 and a second end 514 located proximate to a base bottom and aligning with an implant receptacle 306 of an implant 300. According to some embodiments, a first end 512 may be configured to receive a base fastener 130 and to secure a base fastener head 132. A base fastener head 132 may be configured to be secured within an angled base channel 510 and may have any shape that permits such a secure seat including, for example, a hex head, a pyramid head, a flat head, a washer head, a hexagon-washer head, and a clock head. As shown in FIG. 10, a base fastener head 132 may be inserted into a recess within the angled abutment base 506. In some embodiments, a base fastener 132 may also be configured such that when inserted and secured into a first end of an angled base channel, the base fastener 132 sits flush against a side of the angled abutment base (e.g., a flat head). According to some embodiments, a bottom edge of a base fastener 130 may be configured to traverse an entire length of an angled base channel 510 and extend into an implant threaded receptacle 306 of an implant 300. The base fastener 130 may be driven into the implant 300 through the use of a driving device, such as a screw or hex driver 550.

In some embodiments, an angled abutment base may be inserted into a dental surgical site through a cavity perpendicular to a patient gum line at a dental surgical site and the angled base fastener may be secured through the angled base channel of the angled abutment base and into an implant through a hole generated by an insertion of the implant (i.e., at an angle 504).

According to some embodiments, an angled abutment base 506 may be configured to encourage and support a desired emergent sulcus profile (e.g., contour). In some embodiments, an angled abutment base 506 may include a scalloped region such that one or more edges of the scalloped region align with the desired emergent sulcus profile. As shown in FIG. 10, the implant 300 is driven into the bone tissue 16, while the angled abutment base 506 is placed primarily within the soft tissue region 14, such as the sulcus.

In some embodiments, an angled abutment base may include a second channel 516, as illustrated in FIG. 10. A second channel 516 may be configured to initiate at a top of an angled abutment base (e.g., at a centerline) and extend into the angled abutment base. A second channel 516, in some embodiments, may be configured to receive at least a portion of a base fastener or a cap fastener 150 and thereby attach (e.g., removably) an angled abutment base to an abutment cap 140. According to some embodiments, a first end of a second channel may be configured to form a receptacle configured to receive a base fastener and to secure a base fastener head. A base fastener head may be configured to be secured within a second channel and may have any shape that permits such a secure seat including, for example, a hex head, a pyramid head, a flat head, a washer head, a hexagon-washer head, and a clock head. In some embodiments, a receptacle and a base fastener may be configured such that when inserted and secured into the base receptacle, the base fastener is secured at a level below that of a base top.

According to some embodiments, a second channel 516, as illustrated in FIG. 10 may be configured to receive a portion of a cap fastener 150, for example a threaded portion of a cap fastener 154.

A dog-leg multiple-piece abutment may include an abutment cap 140. In some embodiments, an abutment cap 140 may be configured to compensate for an insertion of an implant at an angle such that a crown may be inserted in a line substantially perpendicular to a patient's gum line. An abutment cap 140, in some embodiments, may include a healing abutment cap, a flat driver cap, a chimney cap, a temporary crown attachment cap, a dog-leg cap, or any combination thereof.

As a tooth replacement process moves to a different surgical stage, a first, attached abutment cap could be removed and replaced with a second abutment cap, the second abutment cap fulfilling a function beneficial to the new surgical stage. The selection of abutment caps, generally built to provide different functions, and the additional capability of swapping of abutment caps from the abutment base generally alleviates the need to remove the patient-specific abutment base supporting a desired and profiled emergent sulcus.

According to some embodiments of the present disclosure one or more patient specific elements of a multiple-piece abutment system may be configured to be attached to a dental surgical site using a guided surgery approach. In some embodiments, a multiple-piece abutment system may include both patient-specific and pre-fabricated elements. For example, a multiple-piece abutment system may include a prefabricated dental implant, a prefabricated healing abutment, a prefabricated specific abutment base, a patient specific angular chimney cap, and a patient specific crown. The example provided is for illustrative purposes only and is does not limit the scope of the present disclosure.

Although the description above contains many embodiments, these should not be construed as limiting the scope of the invention but as merely providing illustrations of some of the presently preferred embodiments of this invention. Thus, the scope of the invention should be determined by the appended claims and their legal equivalents rather than by the examples given.

The invention claimed is:

1. A multiple-piece abutment, comprising:
 (a) an abutment base configured to attach to a dental implant, wherein the abutment base comprises:
   (i) a base top defining a first channel extending along a first axis,
   (ii) an angled base bottom, wherein the base bottom defines a second channel extending along a second axis, wherein the first axis and the second axis define an oblique angle, and
   (iii) a side surface extending from the base top to the base bottom, wherein the second channel extends into the side surface;
 (b) a base fastener configured extend through into the second channel of the angled base bottom via the side surface to couple the abutment base with the dental implant;
 (c) an abutment cap configured to removably attach to an abutment base, wherein the abutment cap defines a cap channel, the abutment cap further comprising a cap bottom projection configured fit within the first channel; and
 (d) a cap fastener configured to extend through the cap channel to attach to the base top via the first channel while the cap bottom projection is housed within the first channel, thereby coupling the abutment cap with the abutment base.

2. The multiple-piece abutment of claim 1, wherein the side surface of the abutment base is configured to support an emergent sulcus, encourage a desired emergent sulcus profile, or both.

3. The multiple-piece abutment of claim 1, wherein the abutment cap is selected from the group consisting of: a healing abutment cap, a chimney cap, a temporary crown attachment cap, a flat driver cap, a dog-leg cap, a cylindrical driver cap, and a driver cap.

4. The multiple-piece abutment of claim 1, wherein the abutment cap is selected from a prefabricated abutment set.

5. The multiple-piece abutment of claim 1, wherein the abutment base comprises an angled abutment base configured to support an emergent sulcus profile.

6. The multiple-piece abutment of claim 1, wherein at least the abutment base is configured to attach to the implant prior to the implant being secured into a dental implant surgical site.

7. The multiple-piece abutment of claim 1, wherein a design of the multiple-piece abutment is generated by a method comprising:
   gathering patient data to generate a first data set;
   creating a virtual model of at least a portion of a patient's mouth by processing the first data set to generate a second data set comprising a first site map and a second site map;
   comparing the first site map and the second site map to generate a comparison data set; and
   using the comparison data set to establish a proposed emergent sulcus profile.

8. A dental implant system for promoting a desired emergent sulcus profile, the system comprising:
   (a) a dental implant comprising an implant receptacle; and
   (b) a multiple-piece abutment configured to attach to an implant, the multiple-piece abutment comprising:
      (i) an abutment base configured to support a desired emergent sulcus profile, wherein the abutment base defines:
         (A) an angled base channel extending along a first axis, and
         (B) a second channel extending along a second axis, wherein the first axis and the second axis define an oblique angle,
      (ii) a base fastener configured to extend through the angled base channel and couple the abutment base with the dental implant via the implant receptacle,
      (iii) an abutment cap configured to removably attach to the abutment base, wherein the abutment cap comprises a cap base configured to rest within the second channel when the abutment cap is attached to the abutment base; and
      (iv) a cap fastener configured to extend within the second channel to couple the abutment cap with the abutment base.

9. The system of claim 8, wherein the abutment cap is selected from the group consisting of: a healing abutment cap, a chimney cap, a temporary crown attachment cap, a flat driver cap, a dog-leg cap, a cylindrical driver cap, and a driver cap.

10. The system of claim 9, wherein the chimney cap comprises a chimney configured to be received by a chimney channel of a crown.

11. The system of claim 10, wherein the crown and the chimney are configured as a single piece.

12. The system of claim 9,
   wherein the abutment cap comprises a flat driver cap comprising a top, and
   wherein the top of the flat driver cap is configured to receive a temporary retainer or a temporary crown.

13. The system of claim 8 further comprising at least one of a crown, a temporary crown, and a temporary retainer.

14. A multiple-piece abutment, comprising:
   (a) an abutment base configured to attach to a dental implant, wherein the abutment base defines a first channel extending along a first axis and a second channel extending along a second axis, wherein the first axis and the second axis define an oblique angle;
   (b) a base fastener configured to extend through the first channel couple the abutment base with the dental implant;
   (c) an abutment cap configured to removably attach to an abutment base, wherein the abutment cap comprises a cap projection configured to rest within the first channel of the abutment base while the abutment cap is attached to the abutment base, wherein the abutment cap defines a cap channel; and
   (d) a cap fastener configured to extend through the cap channel and the second channel to couple the abutment cap with the abutment base.

15. The multi-piece abutment of claim 14, wherein the abutment cap comprises a shoulder defining a portion of the cap channel.

16. The multi-piece abutment of claim 15, wherein the cap fastener comprises a cap faster head configured to rest on the shoulder should of the abutment cap.

17. The multi-piece abutment of claim 14, wherein the abutment cap extends between a cap top and a cap bottom.

18. The multi-piece abutment of claim 17, wherein the cap bottom defines a portion of the cap channel.

19. The multi-piece abutment of claim 14, wherein the abutment base comprises a scalloped surface.

* * * * *

UNITED STATES PATENT AND TRADEMARK OFFICE
CERTIFICATE OF CORRECTION

| | |
|---|---|
| PATENT NO. | : 10,952,824 B2 |
| APPLICATION NO. | : 15/667575 |
| DATED | : March 23, 2021 |
| INVENTOR(S) | : Daniel R. Llop |

It is certified that error appears in the above-identified patent and that said Letters Patent is hereby corrected as shown below:

In the Claims

Column 26, Claim 16, Lines 33-35, "The multi-piece abutment of claim 15, wherein the cap fastener comprises a cap fastener head configured to rest on the shoulder should of the abutment cap."; should be deleted and replaced with "The multi-piece abutment of claim 15, wherein the cap fastener comprises a cap fastener head configured to rest on the shoulder of the abutment cap."

Signed and Sealed this
Fourteenth Day of June, 2022

Katherine Kelly Vidal
*Director of the United States Patent and Trademark Office*